(12) United States Patent
Torii (10) Patent No.: US 8,308,634 B2
(45) Date of Patent: Nov. 13, 2012

(54) ENDOSCOPE

(75) Inventor: Yuichi Torii, Saitama (JP)

(73) Assignee: Fujifilm Corporation, Tokyo (JP)

( * ) Notice: Subject to any disclaimer, the term of this patent is extended or adjusted under 35 U.S.C. 154(b) by 968 days.

(21) Appl. No.: 12/357,136

(22) Filed: Jan. 21, 2009

(65) Prior Publication Data

US 2009/0192357 A1 Jul. 30, 2009

(30) Foreign Application Priority Data

Jan. 22, 2008 (JP) ................. P2008-011323

(51) Int. Cl.
*A61B 1/00* (2006.01)

(52) U.S. Cl. ......... 600/149; 600/146; 600/147; 600/150

(58) Field of Classification Search ................... 600/149
See application file for complete search history.

(56) References Cited

U.S. PATENT DOCUMENTS

| | | | |
|---|---|---|---|
| 4,294,233 A * | 10/1981 | Takahashi | 600/149 |
| 4,483,326 A * | 11/1984 | Yamaka et al. | 600/149 |
| 4,688,555 A * | 8/1987 | Wardle | 600/149 |
| 4,762,119 A * | 8/1988 | Allred et al. | 600/149 |
| 5,299,559 A * | 4/1994 | Bruce et al. | 600/141 |
| 5,331,948 A * | 7/1994 | Utsumi et al. | 600/121 |
| 5,762,067 A | 6/1998 | Dunham et al. | |
| 2002/0017515 A1 | 2/2002 | Obata et al. | |
| 2006/0074383 A1 | 4/2006 | Boulais | |

FOREIGN PATENT DOCUMENTS

| | | |
|---|---|---|
| JP | 02-283347 | 11/1990 |
| JP | 03-292928 | 12/1991 |
| JP | 07-303601 | 11/1995 |
| JP | 8-160317 A | 6/1996 |
| JP | 2000-051146 | 2/2000 |
| WO | WO 2006/126265 A1 | 11/2006 |

* cited by examiner

*Primary Examiner* — Matthew J Kasztejna
(74) *Attorney, Agent, or Firm* — Birch, Stewart, Kolasch & Birch, LLP (57) ABSTRACT

An endoscope includes an insertion portion which has a bending portion, a wire which is fixed to an end of a distal side of the bending portion and is pushed along the insertion portion, an operating portion which is provided on a proximal side of the insertion portion opposite to the bending portion, and a wire-connecting member which is interposed in the wire between the insertion portion and the operating portion to form an allowance in a in which the wire is pushed and pulled, wherein a portion of the wire between the wire-receiving member and the wire-connecting member is inserted into the coil spring so that the coil covers a surface of the portion of the wire.

4 Claims, 11 Drawing Sheets

ENDOSCOPE

The present invention claims priority from Japanese Patent Application No. 2008-011323 filed on Jan. 22, 2008, the entire content of which is incorporated herein by reference.

BACKGROUND OF INVENTION

1. Field of the Invention

The present invention relates to an endoscope having a bending portion capable of being bent by wires, and particularly, to an improved technique of preventing meandering of the wires.

2. Description of the Related Art

An endoscope is composed roughly of an insertion portion inserted into an abdominal cavity or the like, and an operating portion to which a proximal end of this insertion portion is connected. In the insertion portion, a distal end including an image pick-up unit or the like, a bending portion which may be bent, and a long flexible portion which constitutes the proximal end of the insertion portion and is connected to the operation portion are sequentially connected toward the operating portion from the distal side. An operating mechanism for operating the bending portion provided in the insertion portion operates the bending portion by push and pull of wires which are arranged in a pair. As for the pair of wires, typically, a driving wire from the insertion portion and an operating wire from an angle knob that is an operating means are connected together within the operating portion (refer to JP-A-7-23892 JP-A-2003-290138).

Figure 12:
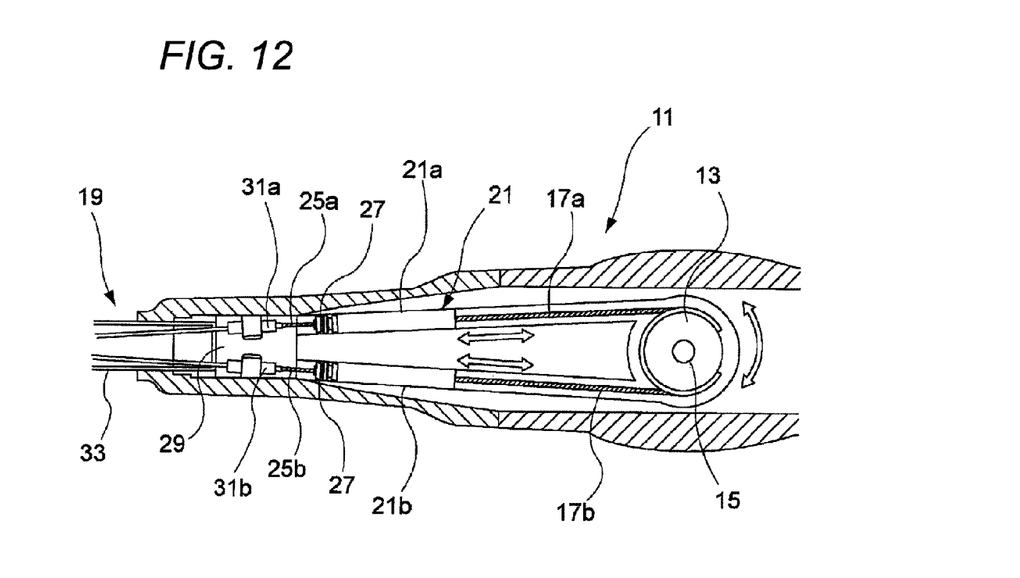
FIG. 12 is a plan view of the inside of an operating portion in an endoscope.

FIG. 12 is a sectional view of an operating portion showing a connection structure in an endoscope.

A pulley 13 is provided inside an operating portion 11, and the pulley 13 is fixed to an angle knob (not shown), which is rotatably provided at a side portion of the operating portion 11, coaxially with a rotary shaft 15. A pair of operating wires 17a and 17b is wound around the pulley 13, and the operating wires 17a and 17b are pushed in the direction of the insertion portion 19, and are connected to one ends of angular pipe-shaped sleeves 21a and 21b that are wire-connecting members 21. Slip-off preventing members 23 (refer to FIGS. 13A and 13B) are respectively housed inside the sleeves 21a and 21b so as to be movable in an axial direction, and ends of the operating wires 17a and 17b are respectively connected to the slip-off preventing members 23. That is, the operating wires 17a and 17b are connected to the sleeves 21a and 21b with the play equivalent to the movement of the slip-off preventing members 23.

Ends of driving wires 25a and 25b are respectively fixed to the other ends of the sleeves 21a and 21b by nut members 27. A bracket 29 is fixed to the portion of the operating portion 11 on the side of the insertion portion 19, and the bracket 29 fixes wire-receiving members 31a and 31b which allow the driving wires 25a and 25b to be movably inserted therethrough. The driving wires 25a and 25b fixed to the sleeves 21a and 21b, respectively, are inserted through the wire-receiving members 31a and 31b, respectively, push in the direction of the tip through a flexible portion 33 of the insertion portion 19, and are connected to a bending portion (not shown) which becomes a distal end of the insertion portion 19. Thereby, when the angle knob is rotated, the operating wires 17a and 17b are pushed or pulled by the pulley 13, the driving wires 25a and 25b are pushed or pulled via the sleeves 21a and 21b correspondingly, and the bending portion of the insertion portion 19 is bent in a predetermined direction.

Figure 13A:
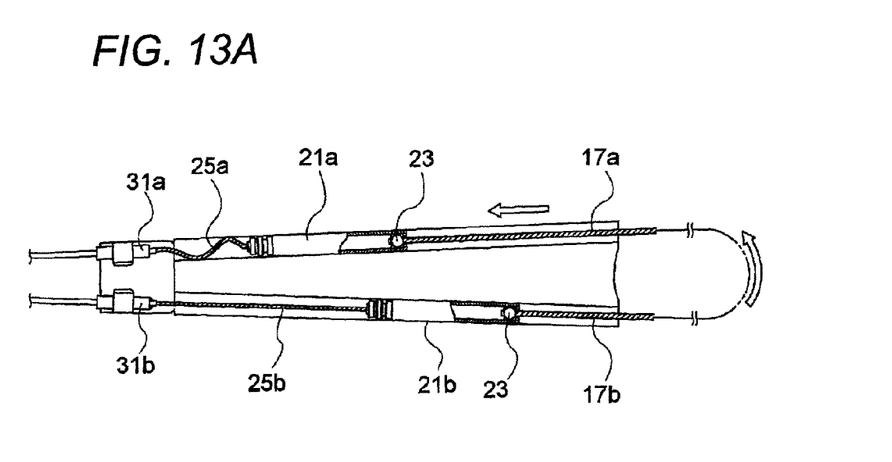
FIG. 13A is a plan view of the inside of the operating portion, showing a wire meandering situation.
Figure 13B:
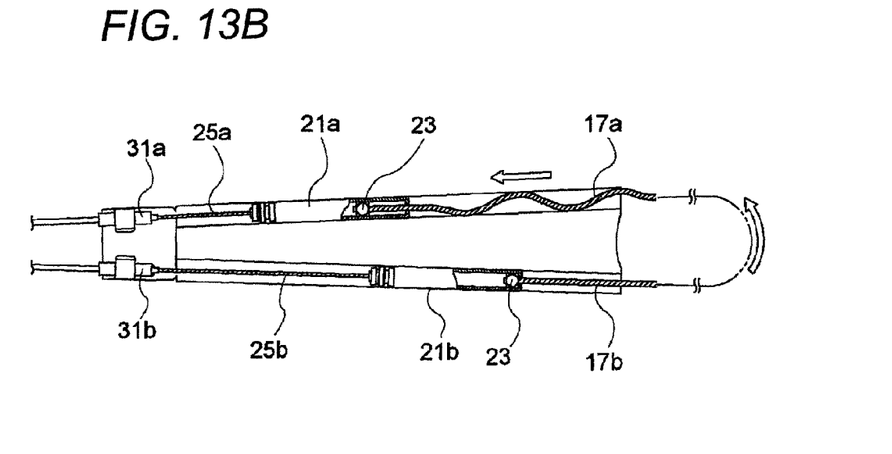
FIG. 13B is a plan view of the inside of the operating portion, showing a wire meandering situation.

However, since the driving wires 25a and 25b and the operating wires 17a and 17b in the endoscope are connected via the sleeves 21a and 21b in the insertion portion 19, and the wires are exposed as they are between the wire-receiving members 31a and 31b and the sleeves 21a and 21b and between the sleeves 21a and 21b and the pulley 13, this connection structure is vulnerable to an axial compressive force. That is, as shown in FIG. 13A, when delivery resistance is stronger at the insertion portion 19 than the wire-receiving members 31a and 31b, the driving wires 25a and 25b between the wire-receiving member 31a and the sleeves 21a meandered due to deflection. On the other hand, as shown in FIG. 13B, when the movement resistance of the sleeves 21a and 21b is great, the operating wire 17a between the sleeve 21a and the pulley 13 meandered due to deflection. If such meandering is repeated frequently, there is a probability that the wires may be damaged by fatigue. In contrast, it is also conceivable that the wires are housed in tubes having rigidity in order to regulate meandering. However, when regions where the wires become naked are eliminated, play may not be given to wire length, and the flexibility of the insertion portion 19 may not be maintained. Additionally, if the sleeves 21a and 21b are interposed, the lengths of the driving wires 25a and 25b between the wire-receiving members 31a and 31b and the sleeves 21a and 21b change with the movement of the sleeves 21a and 21b. Therefore, the structure becomes complicated.

SUMMARY OF INVENTION

The invention is made in consideration of the above situations, and an object of the invention is to provide an endoscope capable of preventing meandering of a bending operating wire by simple structure, and thereby, preventing any damage of the wire.

The above object according to the invention is achieved by the following configurations.

According to a first aspect of the invention, an endoscope includes an insertion portion which has a bending portion, a wire which is fixed to an end of a distal side of the bending portion and is pushed along the insertion portion, an operating portion which is provided on a proximal side of the insertion portion opposite to the bending portion, the operating portion configured to perform a push and pull operation of the wire, a wire-connecting member which is interposed in the wire between the insertion portion and the operating portion to form an allowance in a in which the wire is pushed and pulled, a wire-receiving member which is arranged on an insertion-portion side of the operating portion, the wire being movably inserted through the wire-receiving member to be movable, and a coil spring, wherein a portion of the wire between the wire-receiving member and the wire-connecting member is inserted into the coil spring so that the coil covers a surface of the portion of the wire.

According to this endoscope, even if one of wires on the operating portion is pushed toward the insertion portion and the reaction force of the push acts on the wire, and the wire is going to deflect, the deflection of the wire is regulated because the outer periphery of the wire is covered with the coil spring between the wire-receiving member and the wire-connecting member. Thereby, meandering of the wire between the wire-receiving member and the wire-connecting member is prevented.

According to a second aspect of the invention, one end of the coil spring is fixed to the wire-receiving member, and the other end of the coil spring is fixed to the wire-connecting member.

According to this endoscope, both ends of the coil spring are fixed to the wire-receiving member and the wire-connecting member. Thereby, even if the distance between the wire-receiving member and the wire-connecting member changes with the push and pull operations of the wire, the length of the coil spring makes a resilient change with this change, and the total wire length between the wire-receiving member and the wire-connecting member is always covered with the coil spring.

According to a third aspect of the invention, the coil spring is fixed in a state where an initial tension is given thereto.

According to this endoscope, the wire-connecting member is pulled toward the wire-receiving member by the initial tension of the coil spring, and a tension always acts on the wire on the side of the operating portion, thereby eliminating any deflection in the wire. This prevents meandering of the operating wire.

According to a forth aspect of the invention, the wire-connecting member connects a driving wire portion that is the wire on the insertion-portion side, and an operating wire portion that is the wire on an operating-portion side together, and wherein the wire-connecting member includes, a sleeve connected to an end of the driving wire portion, and a slip-off preventing member that is connected to the operating wire, is movable in the direction of push and pull within the sleeve, and is accommodated in the sleeve, and the sleeve and the split-off preventing member form a slip-off preventing structure that prevents the operating wire from slipping off from the sleeve.

According to this endoscope, the slip-off preventing member moves to a range within the sleeve when the operating wire is pushed toward the insertion portion. This movement becomes a play, and consequently the flexibility of the insertion portion is maintained.

According to a fifth aspect of the invention, a compression spring member arranged within the sleeve and biased the slip-off preventing member toward the operating wire.

According to this endoscope, when the operating wire is pushed, and the driving wire is pushed via the wire-connecting member, the slip-off preventing member of the operating wire presses and compresses the compression spring member within the wire-connecting member. Additionally, since the compression spring member pushes the slip-off preventing member back to the operating portion by its restoring force when operation is stopped, a gap is eliminated between the slip-off preventing member and the wire-connecting member. This enhances the response when the operating wire is pulled. Additionally, even when the operating wire is pushed toward the insertion portion, the slip-off preventing member may move within the wire-connecting member to absorb the amount of sagging of the driving wire.

According to the endoscope related to the invention, when a wire on the operating portion is pushed toward the insertion portion, the deflection of the wire is regulated because the outer periphery of the wire is covered with the coil spring between the wire-receiving member and the wire-connecting member even if the reaction force of the extension acts on the wire, and the wire is going to deflect. Thereby, with simple structure, meandering of the bending operating wire may be prevented, and any damage of the wire may be prevented.

Other aspects and advantages of the invention will be apparent from the following description and the appended claims.

DESCRIPTION OF EXEMPLARY EMBODIMENTS

Hereinafter, preferred embodiments of an endoscope according to the invention will be described in detail with reference to the accompanying drawings.

Figure 1:
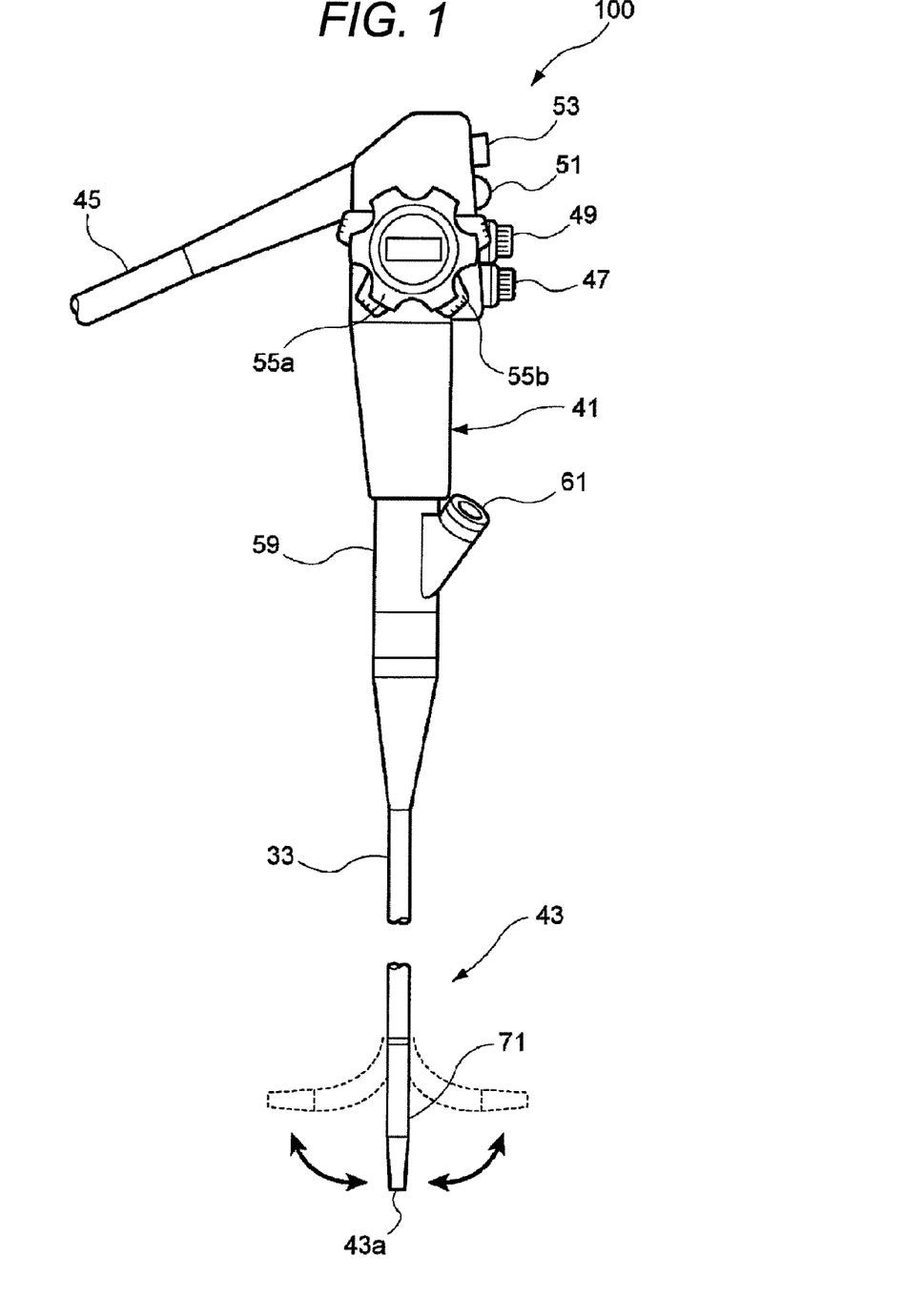
FIG. 1 is an entire configuration diagram of an endoscope according to a first embodiment of the invention.
Figure 2:
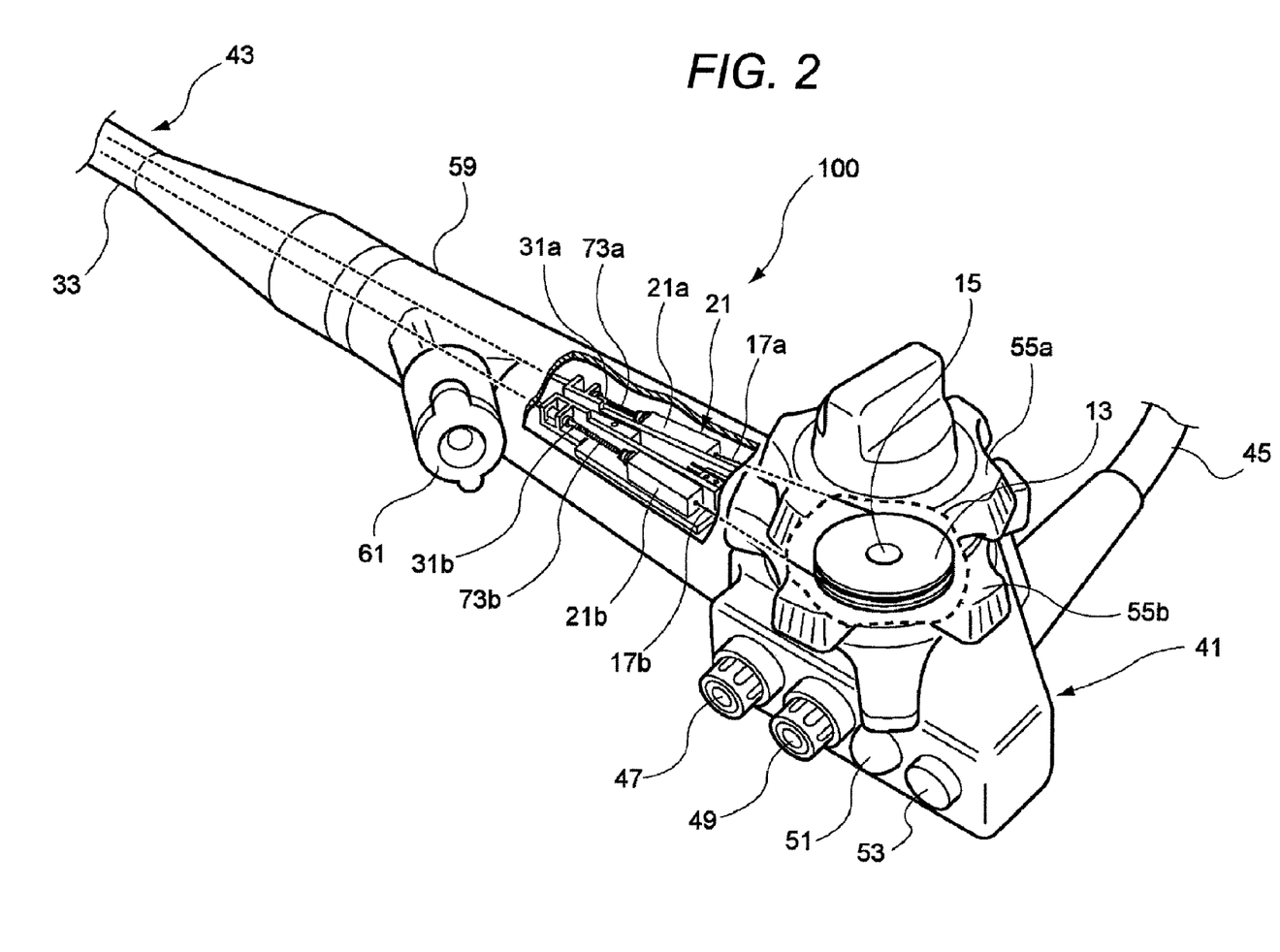
FIG. 2 is a partially cutaway perspective view of an operating portion shown in FIG. 1.

FIG. 1 is an entire configuration diagram of an endoscope according to a first embodiment of the invention, and FIG. 2 is a partially cutaway perspective view of an operating portion shown in FIG. 1. In addition, description will be made with the same reference numerals being given to the same members as the members shown in FIG. 12.

An endoscope 100 includes an operating portion 41, and an insertion portion 43 connected to the operating portion 41 and inserted into an abdominal cavity. A universal cable 45 is connected to the operating portion 41, and a light guide connector (not shown) is provided at the tip of the universal cable 45. The light guide connector is detachably connected to a light source, and illumination light is sent to an illumination optical system at a tip 43a of the insertion portion. Additionally, an electrical connector is connected to the light guide connector, and this electrical connector is detachably connected to a processor.

An air supply/water supply button 47, a suction button 49, a shutter button 51, and a function switching button 53 are provided in parallel in the operating portion 41, and angle knobs 55a and 55b that are a pair of operating means are provided in the operating portion. The operating portion 41 is formed with a connecting portion 59 connected to the insertion portion 43, and the connecting portion 59 has a forceps insertion portion 61. By inserting a treatment instrument, such as forceps, into forceps insertion portion 61, this treatment instrument is led out from a forceps port (not shown) of the tip 43a of the insertion portion.

A pulley 13 is provided inside the operating portion 41, and the pulley 13 is fixed to one, for example, angle knob 55a coaxially with a rotary shaft 15. A pair of operating wires 17a and 17b that are bending operating wires is wound around the pulley 13, and the operating wires 17a and 17b are connected to angular pipe-shaped sleeves 21a and 21b that are wire-connecting members 21 arranged on the side of the insertion portion 43.

Figure 3:
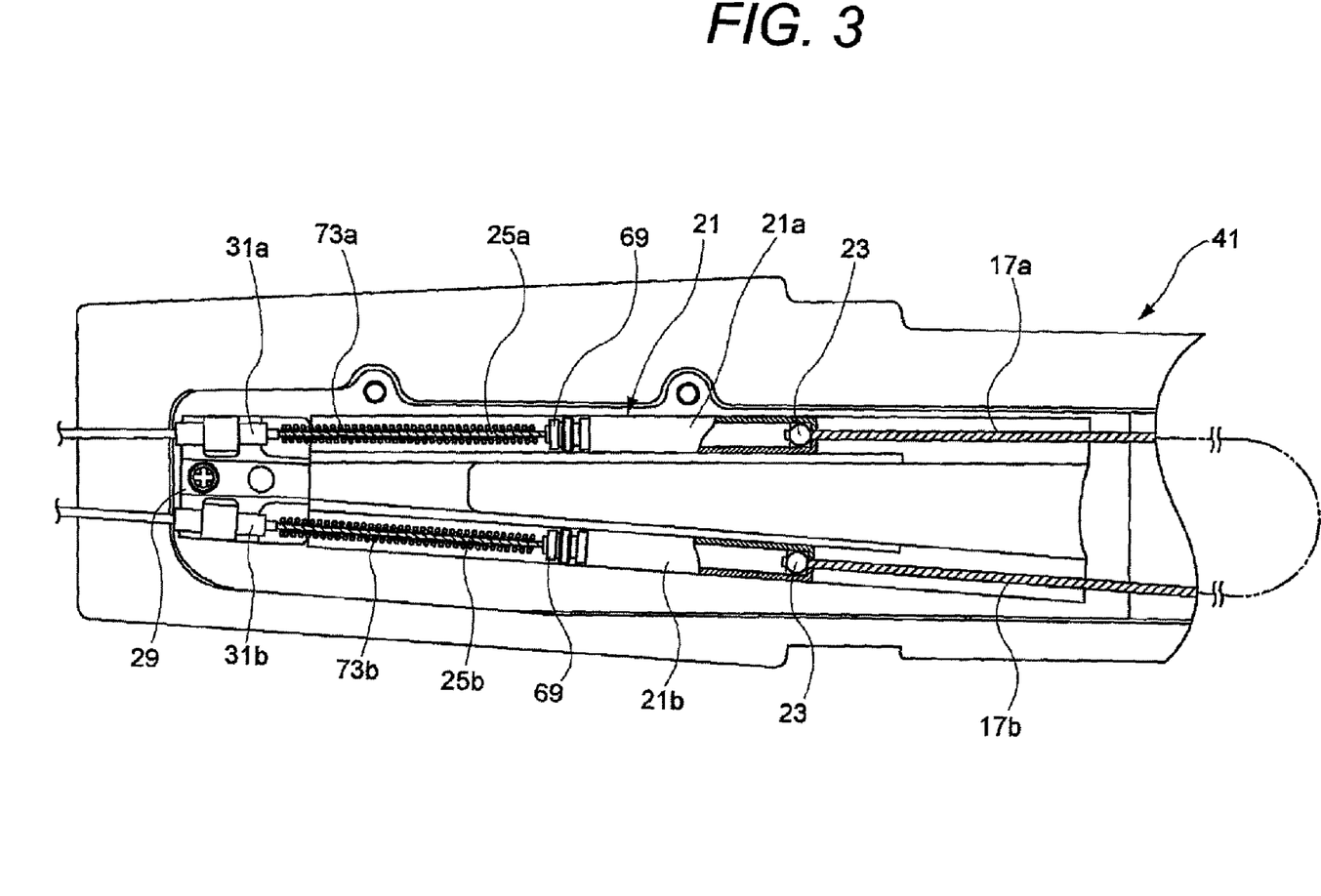
FIG. 3 is an enlarged plan view of the inside of the operating portion shown in FIG. 2.

FIG. 3 is an enlarged plan view of the inside of the operating portion shown in FIG. 2.

Slip-off preventing members 23 are respectively housed inside the sleeves 21a and 21b so as to be movable in an axial direction, and the slip-off preventing members are respectively connected to ends of the operating wires 17a and 17b. That is, the operating wires 17a and 17b are connected to the sleeves 21a and 21b with the play equivalent to the movement of the slip-off preventing members 23. Ends of driving wires 25a and 25b that are bending operating wires are respectively fixed to the other ends of the sleeves 21a and 21b.

Here, the wire connection structure by the sleeves 21a and 21b will be described in more detail.

Figure 4:
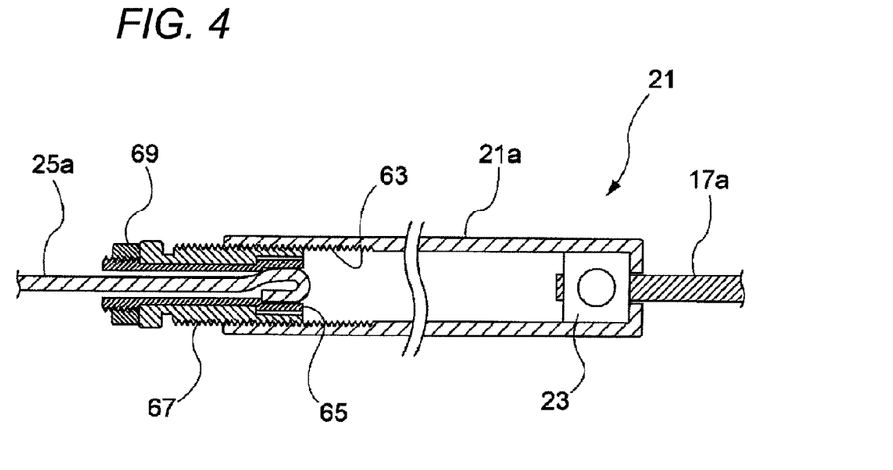
FIG. 4 is a sectional view of a sleeve.

FIG. 4 is a sectional view of a sleeve. Since the connection structures of the sleeves 21a and 21b are the same, one sleeve 21a will be described here as an example. The sleeve 21a is angular pipe-shaped, and has inside dimensions such that the sleeve may house the slip-off preventing member 23. An opening at one end of the sleeve 21a is made narrower than the slip-off preventing member 23, and the operating wire 17a may be inserted through the opening, but the slip-off preventing members 23 does not slip off. The operating wire 17a is connected to the sleeve 21a by such a slip-off preventing mechanism without being separated from the sleeve.

The operating wire 17a becomes movable in the axial direction within the sleeve 21a. A threaded portion 63 is formed in an inner wall of the sleeve 21a opposite the aforementioned slip-off preventing mechanism. The tip of the driving wire 25a is anchored to an engaging tube 65 by soldering or the like. The engaging tube 65 is inserted into a screw member 67, and the screw member 67 is screwed to the threaded portion 63 of the sleeve 21a. The end of the engaging tube 65 opposite the sleeve 21a protrudes from the screw member 67, and a threaded groove is formed at an outer periphery of the protruding portion. The engaging tube 65 is fixed to the screw member 67 as a nut 69 is screwed to the threaded groove. On the other hand, the end of the engaging tube 65 on the side of the sleeve 21a is prevented from slipping out by making its enlarged diameter portion abut on a stepped portion of the screw member 67.

By adopting the above configuration as the connection structure of the operating wire 17a and the driving wire 25a, the driving wire 25a is fixed to the sleeve 21a, the operating wire 17a becomes movable with respect to the sleeve 21a. As a result, the driving wire 25a and the operating wire 17a are connected with the play equivalent to the movement of the slip-off preventing member 23.

A bracket 29 shown in FIG. 3 is fixed to the portion of the operating portion 41 on the side of the insertion portion 43, and the bracket 29 fixes wire-receiving members 31a and 31b which allow the driving wires 25a and 25b to be movably inserted therethrough. The driving wires 25a and 25b fixed to the sleeves 21a and 21b, respectively, are inserted through the wire-receiving members 31a and 31b, respectively, push in the direction of the tip through a flexible portion 33 (refer to FIG. 1) of the insertion portion 43, and are connected to a bending portion 71 at their ends. Thereby, when the angle knob 55a is rotated, the operating wires 17a and 17b are pushed or pulled by the pulley 13, the driving wires 25a and 25b are pushed or pulled via the sleeves 21a and 21b correspondingly, and the bending portion 71 of the insertion portion 43 is bent in a predetermined direction.

The angle knob 55a bends the bending portion 71 right and left. On the other hand, the angle knob 55b bends the bending portion 71 up and down. The pulley, operating wire, sleeve, and driving wire (not shown) as the above ones are connected to the angle knob 55b, and these wire-connecting members are disposed at a lower layer of the connection structure shown in FIG. 2 (not shown). In such connection structure, the slip-off preventing member 23 moves to a range within the sleeve 21a, for example, when the operating wire 17a is pushed toward the insertion portion 43. This movement becomes a play, and consequently the smooth bending of the bending portion 71 is enabled.

A coil spring 73a or 73b which cover wire surfaces are externally inserted onto the driving wire 25a or 25b between the wire-receiving member 31a or 31b and the sleeve 21a or 21b. As the coil springs 73a and 73b, for example, coil springs obtained by spirally winding a wire rod with a circular cross-section may be used. In this embodiment, the ends of the coil springs 73a and 73b become free ends which are not fixed only by covering the coil springs on the outer peripheries of the driving wires 25a and 25b. It is preferable that the internal diameter of the coil springs 73a and 73b be larger than a wire diameter to such an extent that sliding resistance with the driving wires 25a and 25b is not produced. Additionally, it is preferable that a gap be formed between pitches of wound wire rods, i.e., a structure where the springs may be retracted in an axial direction.

Figure 5:
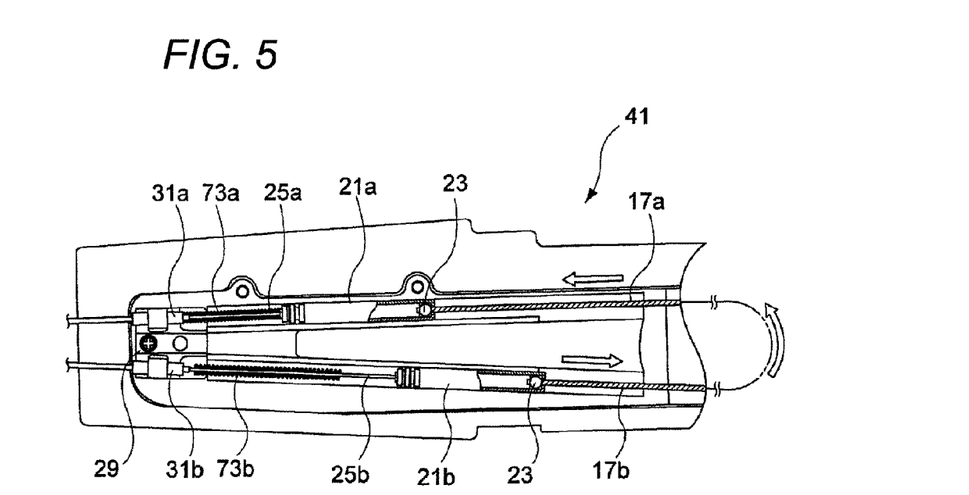
FIG. 5 is an explanatory view of the operation of the first embodiment.

FIG. 5 is an explanatory view of the operation of the first embodiment.

In the above configuration, for example, when the angle knob 55a is operated and the pulley 13 is rotated counterclockwise, the lower operating wire 17b is delivered to the right of FIG. 5, and the slip-off preventing members 23 moves to the right, and the sleeve 21b moves to the right. At this time, the bending portion is bent, and accordingly, the upper operating wire 25a is pulled from the insertion portion 43 (refer to FIGS. 1 and 2). Thereby, the driving wire 25a pressed by the sleeve 21a is introduced into the wire-receiving member 31a, and is pushed to the insertion portion 43. In this case, even if the reaction force of the push in the insertion portion 43 acts on the driving wire 25a, and the driving wire 25a is going to deflect, the outer periphery of the wire is covered with the coil spring 73a between the wire-receiving member 31a and the sleeve 21a, and the deflection is regulated. If the distance between the wire-receiving member 31a and the sleeve 21a becomes shorter than the total length of the coil spring 73a, the coil spring 73a will cover the total length of the driving wire 25a while being compressed.

Accordingly, according to the above endoscope 100, the coil springs 73a and 73b are externally inserted onto the driving wires 25a and 25b between the wire-receiving members 31a and 31b, which are fixed to the portion of the operating portion 41 on the side of the insertion portion 43 and allows the driving wires 25a and 25b to be movably inserted therethrough, and the sleeves 21a and 21b. Thus, when any one of the operating wires 17a and 17b on the side of the operating portion 41 is pushed toward the insertion portion 43, the deflection is regulated because the outer peripheries of the wires are covered with the coil springs 73a and 73b even if the reaction force of the push acts on the driving wires 25a and 25b and any one of the driving wires 25a and 25b is going to deflect. Thereby, with simple structure, meandering of the driving wires 25a and 25b may be prevented, and any damage of the wires may be prevented.

Next, a second embodiment of the endoscope according to the invention will be described.

Figure 6:
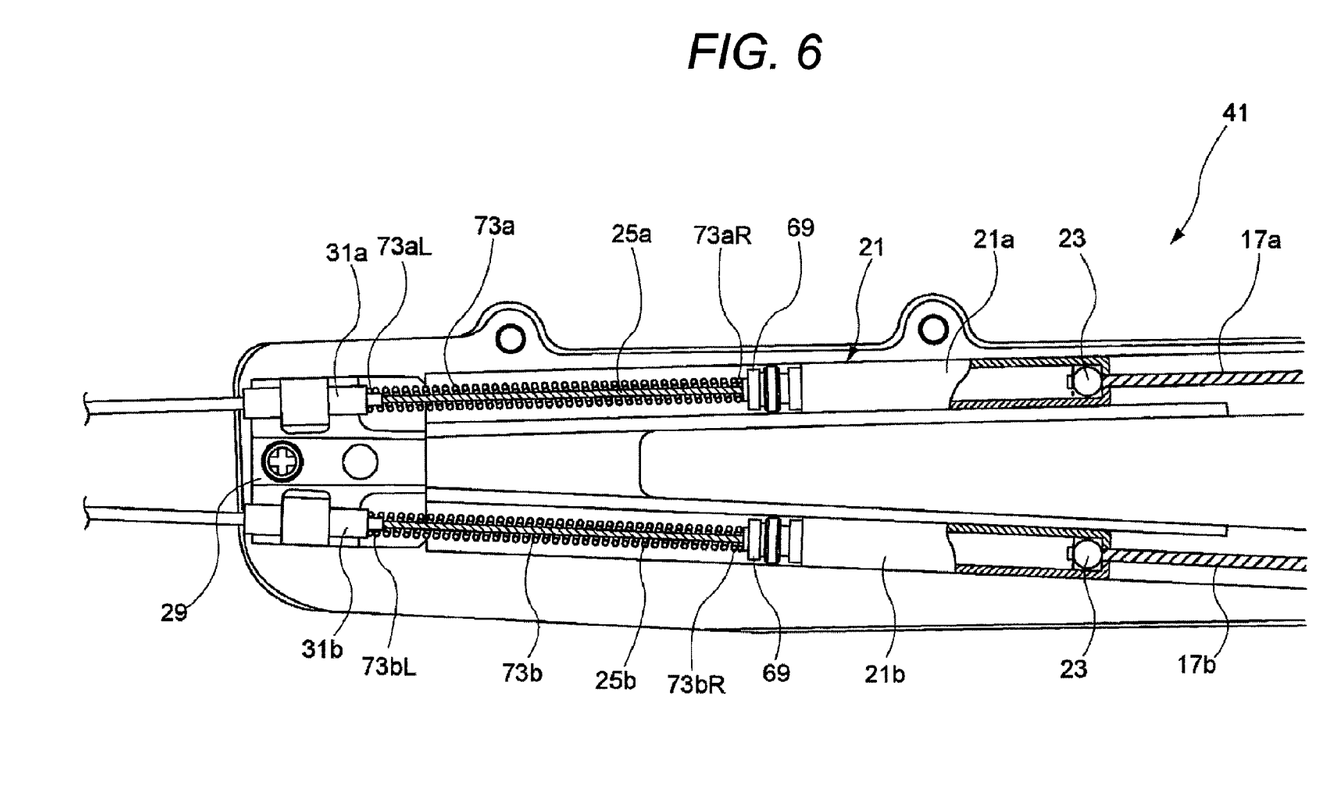
FIG. 6 is an enlarged plan view of the inside of an operating portion according to a second embodiment to which coil springs are fixed.
Figure 7:
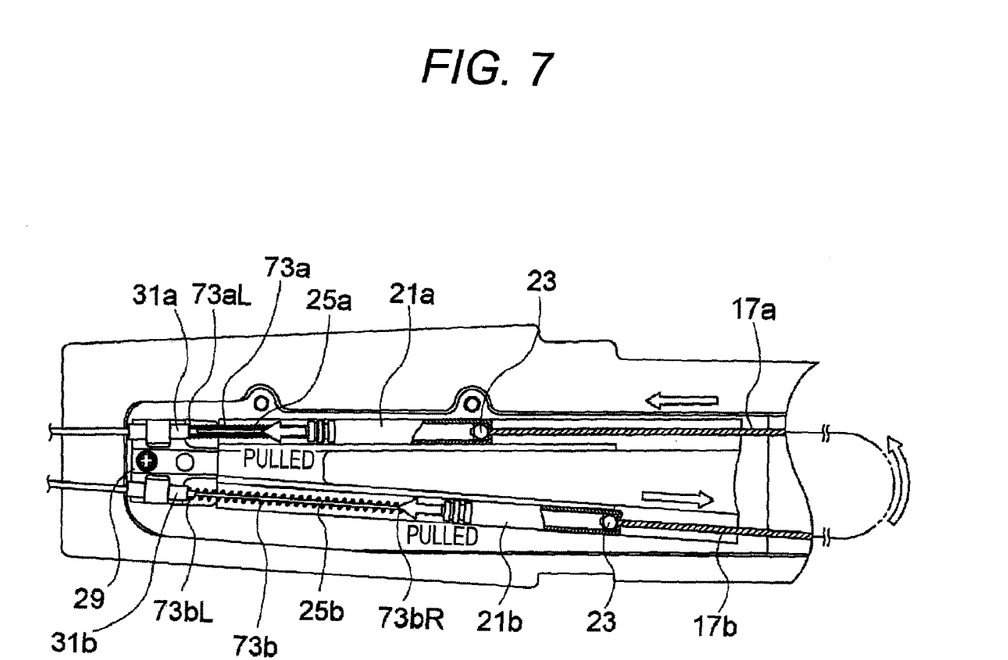
FIG. 7 is an explanatory view of the operation of the second embodiment.

FIG. 6 is an enlarged plan view of the inside of an operating portion according to the second embodiment to which coil springs are fixed, and FIG. 7 is an explanatory view of the operation of the second embodiment. In addition, in the following respective embodiments, the same reference numerals will be given to the same members as the members shown in FIGS. 1 to 5, and duplicate description will be omitted. In this endoscope, one ends (left ends) 73aL and 73bL of the coil springs 73a and 73b are fixed to the wire-receiving members 31a and 31b, respectively, and the other ends (right ends) 73aR and 73bR thereof are fixed to the sleeves 21a and 21b, respectively.

According to this endoscope, both ends of the coil springs 73a and 73b are fixed to the wire-receiving members 31a and 31b and the sleeves 21a and 21b. Thereby, even if the distance between the wire-receiving members 31a and 31b and the sleeves 21a and 21b changes with the push and pull operations of the wires, the length of the coil springs 73a and 73b makes a resilient change with this change, and the total wire lengths between the wire-receiving members 31a and 31b and the sleeves 21a and 21b are always covered with the coil springs 73a and 73b.

In this embodiment, the fixation may be made with an initial tension being further given to the coil springs 73a and 73b. That is, both the coil springs 73a and 73b are made to have an initial tension and are fixed in an equilibrium state shown in FIG. 6 such that the sleeves 21a and 21b are drawn toward the wire-receiving member 31a and 31b. In this case, as shown in FIG. 7, when the angle knob 55a is operated and the operating wire 17a is pushed to the left, the sleeve 21a is pulled toward the wire-receiving member 31a by the initial tension of the coil springs 73a and 73b, and the sleeve 21a moves to the left. Then, the slip-off preventing member 23 is kept abutting on the right end of the sleeve 21a. Thereby, a tension always acts on the operating wire 17a, and thus, any deflection is not produced and meandering of the operating wire 17a is prevented. In addition, although the coil spring 73b pulls the sleeve 21b in a direction reverse to its pushed direction, the operating force by the angle knob 55a is sufficiently larger than this pull force, and therefore, there is no particular hindrance.

Next, a third embodiment of the endoscope according to the invention will be described.

Figure 8:
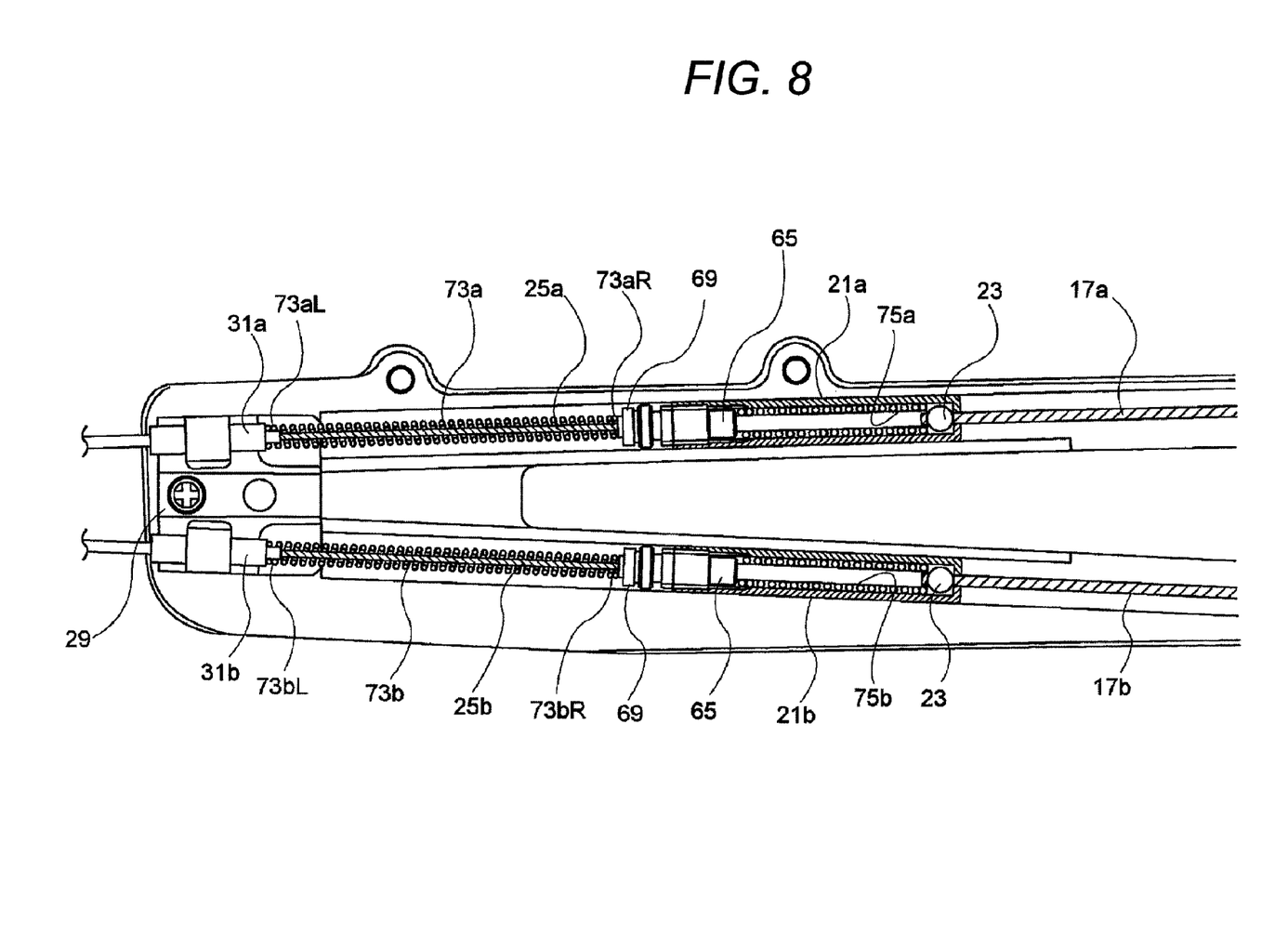
FIG. 8 is an enlarged plan view of the inside of an operating portion according to a third embodiment in which compression spring members are provided inside sleeves, respectively.
Figure 9:
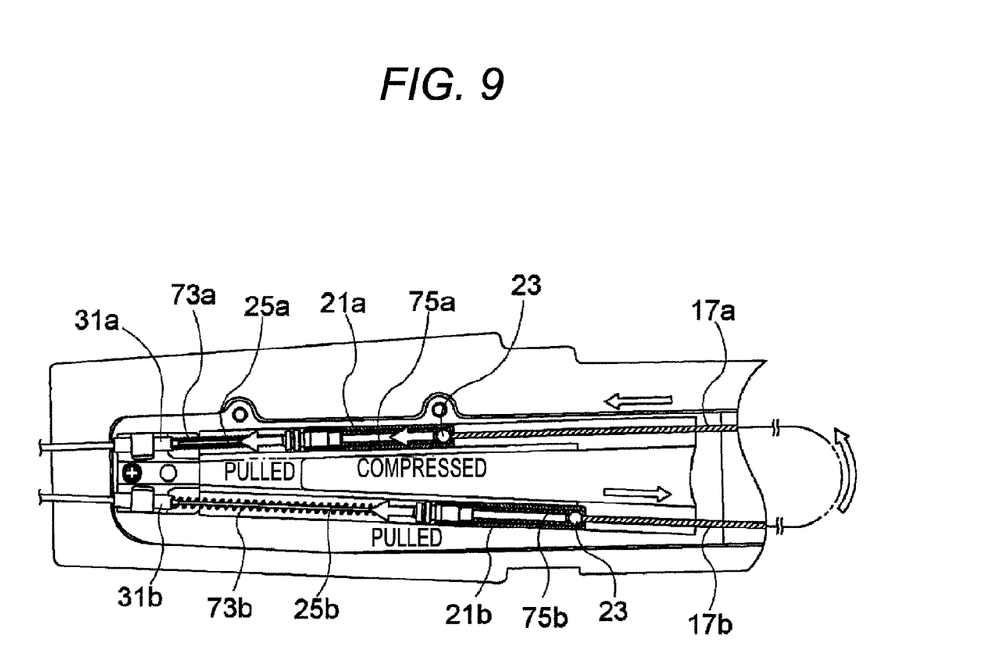
FIG. 9 is an explanatory view of the operation of the third embodiment.

FIG. 8 is an enlarged plan view the inside of an operating portion according to the third embodiment in which compression spring members are provided inside sleeves, respectively, FIG. 9 is an explanatory view of the operation of the third embodiment, and FIG. 10 is an explanatory view showing the operation of a compression spring member.

In this endoscope, as shown in FIG. 8, compression spring members 75a and 75b which biases the slip-off preventing members 23 toward the operating wires 17a and 17b are provided inside the sleeves 21a and 21b, respectively. The compression spring members 75a and 75b may be coil springs which are housed in a compressed state. A left end of each spring member abuts on the engaging tube 65, and the other end thereof abuts on the slip-off preventing member 23. The compression spring members 75a and 75b may be proper spring members, such as leaf springs, besides the coil springs.

Figure 10A:
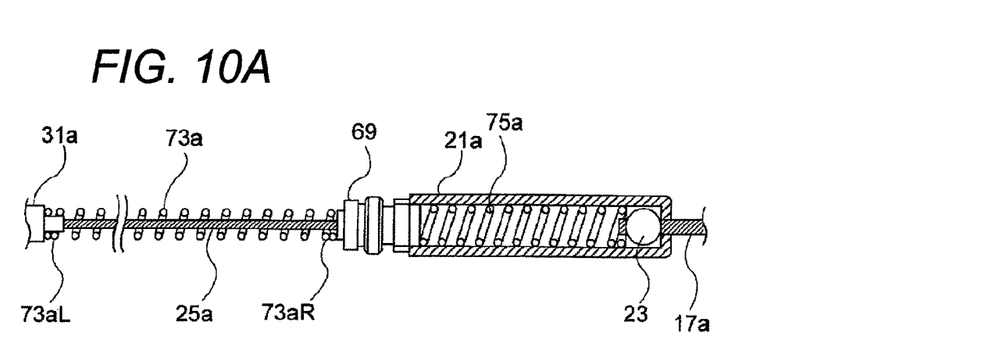
FIG. 10A is an explanatory view showing the operation of a compression spring member.
Figure 10B:
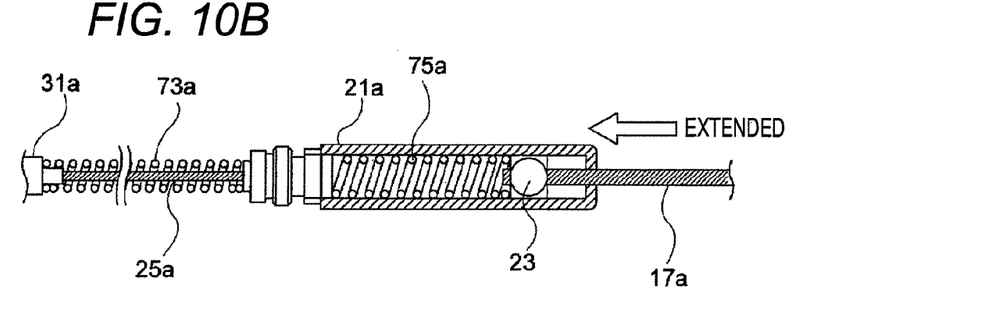
FIG. 10B is an explanatory view showing the operation of a compression spring member.

According to this endoscope, as shown in FIG. 9, for example, when the operating wire 17a is delivered and the driving wire 25a is pushed via the sleeve 21a, the slip-off preventing member 23 of the operating wire 17a presses the compression spring member 75a within the sleeve 21a. When a pressing force on the side of the insertion portion (left direction) is applied to the slip-off preventing member 23 as shown in FIG. 10A, the driving wire 25a is pushed while the compression spring member 75a is once compressed as shown in FIG. 10B.

Figure 10C:
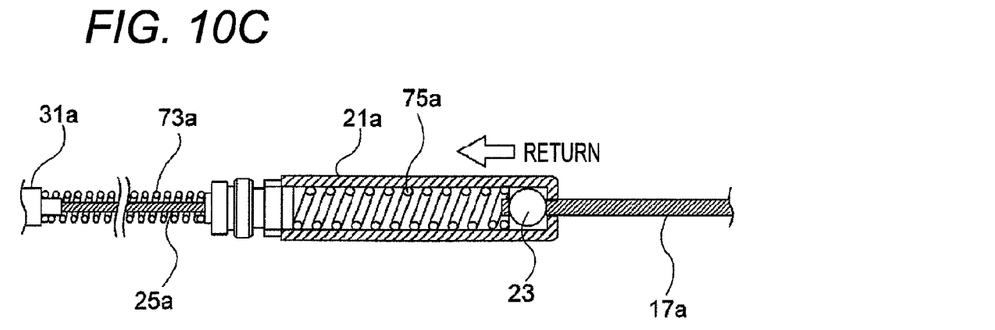
FIG. 10C is an explanatory view showing the operation of a compression spring member.
Figure 10D:
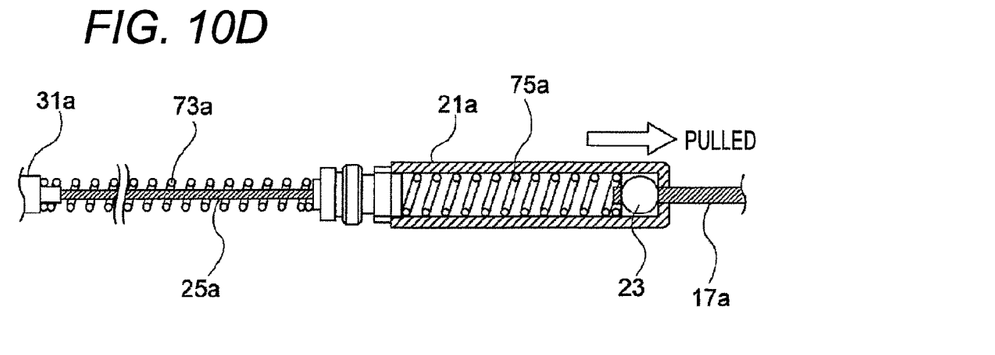
FIG. 10D is an explanatory view showing the operation of a compression spring member.

Almost simultaneously with stop of the extension, the sleeve 21a is pulled back to the insertion portion (left side) as shown in FIG. 10C by the restoring force of the compression spring member 75a, and a gap is eliminated between the slip-off preventing member 23 and the sleeve 21a. Thereby, as shown in FIG. 10D, the response when the operating wire 17a is pulled toward the operating portion (right side) is increased. Additionally even by this configuration, the sagging amount of the operating wire 17a which is caused when the operating wire 17a is pushed toward the insertion portion (left side) is absorbed as the slip-off preventing members 23 moves within the sleeve 21a.

Figure 11:
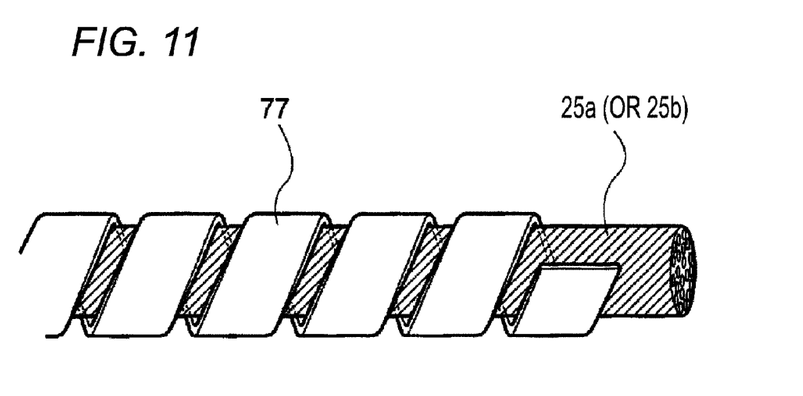
FIG. 11 is a side view showing a modification of the coil spring.

In addition, although coil spring formed by spirally winding wire rods with a circular cross-section are used as the coil springs 73a and 73b in the above embodiment, the invention is not limited thereto, and other types of springs may also be applied. FIG. 11 is a side view showing a modification of the coil spring. The coil spring may also be, for example, a coil spring 77 formed by spirally winding a strip material having a spring property shown in FIG. 11. By using the coil spring 77 made of such a strip material, the area of contact with the driving wires 25a and 25b may be increased, thereby guiding the driving wires 25a and 25b so as to more hardly deflect, and consequently, making it harder to cause meandering.

What is claimed is:

1. An endoscope comprising:
an insertion portion which has a bending portion;
a wire which is fixed to an end of a distal side of the bending portion and is pushed along the insertion portion,
an operating portion which is provided on a proximal side of the insertion portion opposite to the bending portion, the operating portion configured to perform a push and pull operation of the wire;
a wire-connecting member which is interposed between the insertion portion and the operating portion to form an allowance in a direction in which the wire is pushed and pulled;
a wire-receiving member which is arranged on an insertion-portion side of the operating portion, the wire being movably inserted through the wire-receiving member to be movable; and
a coil spring, wherein a portion of the wire between the wire-receiving member and the wire-connecting member is inserted into the coil spring so that the coil covers a surface of the portion of the wire; and
wherein the wire-connecting member connects a driving wire portion that is the wire on the insertion-portion side, and an operating wire portion that is the wire on an operating-portion side together, and
wherein the wire-connecting member includes,
a sleeve connected to an end of the driving wire portion, and
a slip-off preventing member that is connected to the operating wire portion, is movable in the direction of push and pull within the sleeve, and is accommodated in the sleeve, and the sleeve and the split-off preventing member form a slip-off preventing structure that prevents the operating wire portion from slipping off from the sleeve.

2. The endoscope according to claim 1, wherein one end of the coil spring is fixed to the wire-receiving member, and the other end of the coil spring is fixed to the wire-connecting member.

3. The endoscope according to claim 2, wherein the coil spring is fixed in a state where an initial tension is given thereto.

4. The endoscope according to claim 1, further comprising: a compression spring member arranged within the sleeve and biased the slip-off preventing member toward the operating wire portion.

* * * * *